United States Patent [19]

Wiedrich et al.

[11] Patent Number: 5,049,385
[45] Date of Patent: Sep. 17, 1991

[54] SOLID HALOGEN-CONTAINING COMPOSITION AND METHOD FOR PRODUCING SAME

[75] Inventors: Charles R. Wiedrich, Wadsworth; Robert B. Simmons, Norton; Jonathan G. Lasch, Akron, all of Ohio

[73] Assignee: PPG Industries, Inc., Pittsburgh, Pa.

[21] Appl. No.: 213,383

[22] Filed: Jun. 30, 1988

[51] Int. Cl.$^5$ .............................. A01N 25/12
[52] U.S. Cl. ....................... 424/408; 422/5; 422/12; 422/16; 422/37; 424/421
[58] Field of Search .............. 422/37, 512, 16; 424/408, 421

[56] References Cited

U.S. PATENT DOCUMENTS

| | | | |
|---|---|---|---|
| 3,342,674 | 9/1967 | Kowalski | 167/42 |
| 3,488,420 | 1/1970 | Keast et al. | 424/128 |
| 3,741,805 | 6/1973 | Crotty et al. | 134/4 |
| 4,104,024 | 8/1978 | Vogele et al. | 21/58 |
| 4,200,606 | 4/1980 | Kitko | 422/37 |
| 4,457,855 | 7/1984 | Sudbury | 252/98 |
| 4,536,367 | 8/1985 | Hung et al. | 422/37 |
| 4,554,091 | 11/1985 | Jones et al. | 252/37 |
| 4,587,069 | 5/1986 | Meloy | 422/37 X |
| 4,597,941 | 7/1986 | Bottom | 422/37 |
| 4,728,498 | 3/1988 | Theeuwes | 422/37 X |
| 4,767,542 | 8/1988 | Worley | 422/37 X |

FOREIGN PATENT DOCUMENTS 128414 12/1984 European Pat. Off. .

*Primary Examiner*—Thurman Page
*Attorney, Agent, or Firm*—Irwin M. Stein

[57] ABSTRACT

Described is particulate halogen-containing material, e.g., calcium hypochlorite, containing from about 0.1 to about 10 weight percent of colorant-treated particulate inorganic water soluble salt, e.g., sodium chloride. The colorant used with the sodium chloride salt is resistant to oxidation by the halogen specie in the material and is water dispersible. The amount of colorant used is from about 0.01 to about 5 weight percent, based on the inorganic salt. Preferred are the water dispersible phthalocyanine colorants.

14 Claims, No Drawings

SOLID HALOGEN-CONTAINING COMPOSITION AND METHOD FOR PRODUCING SAME

DESCRIPTION OF THE INVENTION

A variety of solid halogen-containing materials are known to serve as disinfecting and/or sanitizing agents. These materials are believed to function as disinfecting agents by virtue of the formation of a hypohalite ion, e.g., hypochlorite ion, or hypohalous acid, e.g., hypochlorous acid, when the material is dissolved in an aqueous medium. Typically, the halogen-containing material is a chlorine, bromine, iodine or chlorine and bromine-containing material. Representative examples of such halogen-containing materials include: the hypochlorites, such as lithium hypochlorite and calcium hypochlorite, chlorinated isocyanuric acids, such as dichloroisocyanuric acid and its sodium and potassium salts, and trichloroisocyanuric acid, the chlorinated and brominated hydantoins, such as 1,3-dibromo-5,5-dimethylhydantoin, the N-halo-2-oxazolidinones, such as 3-chloro-4,4-dimethyl-2-oxazolidinone, and N,N'-dihalo-2-imidazolidinones, such as 1,3-dichloro4,4,5,5,-tetramethyl-2-imidazolidinone.

Calcium hypochlorite enjoys a major portion of the market for available chlorine compounds because it is the cheapest and most stable solid composition known which delivers all of its available chlorine immediately on contact with oxidizable materials. Calcium hypochlorite compositions containing at least 65 weight percent available chlorine, e.g., granular calcium hypochlorite compositions, have been on the market for many years and are used primarily as a disinfecting and sanitizing agent, particularly in the disinfection and sanitizing of water supplies, such as swimming pool water. Solid formed articles prepared from calcium hypochlorite compositions, e.g., tablets, have also been on the market for many years. Such tablets provide a continuous source of available chlorine for disinfecting and sanitizing water supplies over a longer period of time than granular calcium hypochlorite.

Each of the aforedescribed commercially available halogen-containing materials are prepared by methods well known to the skilled artisan. Commonly, such materials are prepared using the same starting reactants (although methods may differ) and, hence, the commercial products resulting from such methods are substantially the same compositionally regardless of the manufacturer. For example, while the commercial processes used for manufacturing calcium hypochlorite from lime and alkali, e.g., sodium hydroxide, may vary from manufacturer to manufacturer, the chemical composition of the resulting calcium hypochlorite products produced by such manufacturers are very nearly the same—varying principally in the level of by-product salts. Commonly, commercially available granular calcium hypochlorite contains calcium hypochlorite, sodium chloride, and water as the principal ingredients. Varying amounts of residual by-product salts, such as sodium chloride, calcium chloride, calcium hydroxide, calcium carbonate and calcium chlorate make up the rest of the product. The physical characteristics of granular calcium hypochlorite from different commercial sources are also similar, albeit some differences do exist.

As a consequence of the aforesaid circumstances, with the exception of the original package or trade dress, similar grades of solid chlorine or bromine-containing compositions, e.g., calcium hypochlorite, are not readily differentiated without resorting to time consuming analytical procedures. It would, however, be beneficial for a manufacturer of such compositions to be able to readily confirm that a particular product is, in fact, its own product.

The present invention relates to solid halogen-containing compositions-having readily discernible chemically-compatible particles dispersed throughout the solid composition, e.g., granular, powder or formed solid. More particularly, the particles dispersed throughout the composition are relatively stable to oxidation by the halogen(s) present in the halogen-containing composition, and are of a different color than the halogen-containing material forming the continuous phase of the composition.

In a particular embodiment, the present invention relates to calcium hypochlorite compositions and, more particularly, relates to granular calcium hypochlorite containing a readily identifiable amount of particulate, dyed inorganic salt that is compatible with the granular calcium hypochlorite. Still more particularly, the present invention relates to granular calcium hypochlorite containing a small amount of particulate sodium chloride that has been treated with a water dispersible phthalocyanine pigment, and to methods for preparing such calcium hypochlorite compositions.

In accordance with the present invention, solid halogen-containing materials, e.g., calcium hypochlorite, containing a readily identifiable particles that do not alter the bleaching or sanitizing functions or performance of the halogen-containing material when used in its typical applications, is provided. More particularly, the particulate material dispersed throughout the solid halogen-containing material is an inorganic salt which contains a colorant, the colored inorganic salt and colorant being resistant to the action of halogen present in the halogen-containing material. Still more particularly, it has been discovered that particulate, e.g., granular or powdery, calcium hypochlorite, (and formed products produced therefrom) can be readily identified by incorporating a small amount of a compatible inorganic salt, e.g., sodium chloride, that has been treated with water-dispersible colorant, the inorganic salt and colorant being resistant to oxidation by calcium hypochlorite.

DETAILED DESCRIPTION OF THE INVENTION

Calcium hypochlorite that may be mixed with a colorant-containing inorganic salt includes any commercially available particulate calcium hypochlorite. Chemically, commercially available calcium hypochlorite typically contains at least about 60 weight percent available chlorine, e.g., between about 60 and about 72 percent available chlorine. Presently, calcium hypochlorite articles of commerce generally contain between about 65 and about 70 weight percent available chlorine. The remainder of such calcium hypochlorite products is usually composed of varying amounts of water, and inorganic by-product calcium and alkali metal salts incorporated during the manufacturing process. Such salts include sodium chloride, calcium chloride, calcium hydroxide, calcium carbonate and calcium chlorate. Water may comprise between about 2 and about 15 percent, e.g., between about 4 and 10 percent, by weight of the calcium hypochlorite product.

The particulate size and particle size distribution of particulate calcium hypochlorite products may vary and often depends on its ultimate use. The particulate size and particle size distribution of the calcium hypochlorite that may be used in the present invention is not critical and thus any particulate material, e.g., from a powdery material to a granular material, may be used to prepare compositions of the present invention. As a general guideline, particulate calcium hypochlorite typically has a principal size distribution between about $-6$ and $+100$ U.S. Sieve Series, i.e., the particles vary in size principally between about 0.13 inches (3.3 millimeters) and about 0.006 inches (0.15 millimeters). More commonly, the particles will have a principal size distribution between about $-6$ and $+60$ (0.25 millimeters) U.S. Sieve.

Calcium hypochlorite compositions described herein may be used to prepare solid formed articles, e.g., tablets, bricks, briquettes, pellets, etc. by conventional size enlargement equipment such as a molding press, tableting press, roll-type press, pellet mill and screw extruder. Particularly suitable for use in producing such solid articles is granular calcium hypochlorite having a size distribution of $-10$ (2.00 millimeters), and $+45$ (0.35 millimeters) U.S. Sieve Series, i.e., the granules are principally between about 0.08 inches and 0.014 inches. Particles smaller than 50 (0.297 millimeters) U.S. Sieve that are present in the granular calcium hypochlorite represent a minor percentage, usually less than 2 percent, of the material charged to a size enlargement device.

Lithium hypochlorite is available commercially as a free-flowing, white granular product containing about 35 percent available chlorine. Major by-products found in lithium hypochlorite include sodium chloride and sodium chloride or potassium sulfate. Minor amounts of lithium chloride, lithium chlorate, lithium hydroxide and lithium carbonate are also found in the product. Water typically comprises about 7 percent by weight of the lithium hypochlorite article of commerce. Granular lithium hypochlorite generally has a particle size between about $-10$ (1.98 millimeters) and $+70$ (0.21 millimeters) U.S. Sieve series.

Chlorinated isocyanurates are a further example of a solid halogen-containing material that may be used to prepare the compositions of the present invention. The two commonly used chlorinated isocyanurates are dichloroisocyanuric acid and its sodium and potassium salts. Dichloroisocyanuric acid is commonly available as the sodium salt in the form of a white granular substance having from about 62 to about 70 percent available chlorine. It is also sold in the dihydrate form. Trichloroisocyanuric acid (sometimes called trichlor for brevity) is a white granular powder or granule which is commercially available containing about 90 percent available chlorine. It is often formulated with cyanuric acid in amounts of about 1 part cyanuric acid to from about 2 to 4 parts of trichlor.

A further group of disinfecting agents that may be used to prepare the compositions of the present invention are the halogenated, i.e., brominated and chlorinated, dimethyl hydantoins, such as 1,3-dibromo-5,5-dimethylhydrantoin, 1,3-dichloro-5,5-dimethylhydantoin and 1-bromo-3-chloro-5,5-dimethylhydrantoin. 1,3-dibromo-5,5-dimethylhydantoin is available commercially as a free-flowing cream colored powder containing about 55 percent active bromine. 1,3-dichloro-5,5-dimethylhydantoin is commercially available as a white powder containing about 36 percent active chlorine. These hydantoins may be prepared respectively by the bromination or chlorination of dimethylhydantoin. 1-bromo-3-chloro-5,5,-dimethylhydantoin is available commercially as a free-flowing white powder containing about 33 percent active bromine and about 14 percent active chlorine. It may be prepared by the sequential chlorination and bromination of dimethylhydantoin.

N-halamines are also halogen-containing materials that may be used to prepare the compositions of the present invention. This group of compounds comprises derivatives of amines in which 1 or 2 nitrogens in the compound are bonded to a halogen, such as chlorine or bromine. Representative examples of such halamine compounds include, chloramine T (sodium-N-chloro-p-toluenesulfonamide). dichloramine-T (N,N-dichloro-p-toluenesulfonamide) 3-halo-2-oxazolidinones and N,N'-dihalo-2-imidazolidinones.

Chloramine T is commercially available as a white or slightly yellow crystal or crystalline powder containing from about 11.5 to about 13 percent active chlorine. Dichloramine-T is available commercially as pale yellow crystals containing from 28 to about 30 percent active chlorine.

The 2-oxazolidinones that may be used to prepare compositions of the present invention may be represented by the following graphic formula,

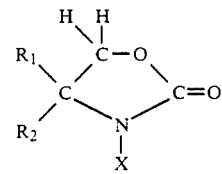

wherein X is chlorine or bromine, $R_1$ is $C_1$–$C_4$ alkyl, such as methyl, ethyl, propyl, isopropyl, butyl, isobutyl and secondary butyl, and $R_2$ is selected from the group $R_1$, i.e., $C_1$–$C_4$ alkyl, hydroxy, hydroxymethyl. $C_1$–$C_4$ alkoxy, such as methoxy, ethoxy, propoxy, isopropoxy and butoxy, e.g., n-butoxy, isobutoxy and secondary butoxy, and substituted phenyl (-Ph-R), particularly para-substituted phenyl, wherein Ph is bivalent substitute phenyl (phenylene) and said phenyl substitutents, R, are each selected from the group consisting of $C_1$–$C_4$ alkyl, $C_1$–$C_4$ alkoxy and hydroxy. Preferably $R_1$ and $R_2$ are a $C_1$–$C_4$ alkyl and, more preferably, are selected from the group consisting of methyl and ethyl, Preferably, $R_1$ and $R_2$ are the same, and still more preferably are methyl.

Examples of 2-oxazolidinones include:
3-chloro-4,4-dimethyl-2-oxazolidinone,
3-chloro-4,4-diethyl-2-oxazolidinone,
3-chloro-4-methyl-4-ethyl-2-oxazolidinone,
3-chloro-4-methyl-4-hydroxy-2-oxazolidinone,
3-chloro-4-methyl-4-methoxy-2-oxazolidinone,
3-chloro-4-methyl-4-hydroxymethyl-2-oxazolidinone, and
3-chloro-4-methyl-4-p-methylphenyl-2-oxazolidinone.
By substitution of other $R_1$ and $R_2$ named substitutents at the 4-position of the -chloro-2-oxazolidinone for the specifically enumerated substitutents listed hereinbefore, other analogous oxazolidinone derivatives may be named. The preferred 2-oxazolidinone is 3-chloro-4,4-dimethyl-2-oxazolidinone.

N-N'-dihalo-2-imidazolidinones that may be used to prepare the compositions of the present invention may be represented by the following graphic formula,

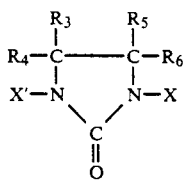

wherein X and X' are each halogen selected from the group chlorine and bromine, $R_3$, $R_4$, $R_5$ and $R_6$ are each selected from the group consisting of hydrogen, $C_1$–$C_4$ alkyl, $C_1$–$C_4$ alkoxy, hydroxy and substituted phenyl, particularly para-substituted phenyl, wherein said phenyl substituents are each selected from the group consisting of $C_1$–$C_4$ alkyl, $C_1$–$C_4$ alkoxy and hydroxy; provided, however, that not more than one of the substituents $R_3$–$R_6$ is hydrogen.

The alkyl substitutents attached to the ring of the 2-imidazolidinone compounds or to the phenyl substituent may contain from 1 to 4 carbon atoms; namely, methyl, ethyl, propyl, isopropyl and the butyls, e.g., n-butyl, isobutyl, and secondary butyl. Similarly, the alkoxy substitutents attached to the ring or the phenyl substituent may contain from 1 to 4 carbon atoms; namely, methoxy, ethoxy, propoxy, isopropoxy and butoxy, e.g., n-butoxy, isobutoxy, and secondary butoxy.

N,N'-dihalo-2-imidazolidinones of the present invention include those in which at least 3 of the 4 substitutents (namely $R_3$–$R_6$) on the carbon atoms at the 4 and 5 positions of the ring are chosen from the described alkyl, alkoxy. hydroxy, or substituted phenyl substituents. Preferably, all four of the substituents are chosen from said group of substituents. Thus, N,N'-dihalo-2-imidazolidinone derivatives contemplated are tri- and tetra-substituted N,N'-dihalo-2-imidazolidinones. More preferably, the $R_3$–$R_6$ substituents and the phenyl substituents are $C_1$–$C_2$ alkyl groups, i.e., methyl and ethyl groups. Still more preferably, $R_3$–$R_6$ are methyl groups.

Examples of the aforedescribed organic compounds include but are not limited to:

1-bromo-3-chloro-4,4,5,5-tetramethyl-2-imidazolidinone;
1,3-dichloro-4,5,5-trimethyl-2-imidazolidinone;
1,3-dichloro-4-methoxy-4,5,5-trimethyl-2-imidazolidinone;
1,3-dibromo-4.4.5,5-tetramethy-2-imidazolidinone;
1,3-dichloro-4,4,5,5-tetramethyl-2-imidazolidinone;
1,3-dichloro-4-hydroxy-4,5,5-trimethyl-2-imidazolidinone;
1,3-dichloro-4-ethyl-4,5,5-trimethyl-2-imidazolidinone;
1,3-dichloro-4,4-diethyl-5,5-dimethyl-2-imidazolidinone; and
1,3-dichloro-4,4,5,5-tetraethyl-2-imidazolidinone.

By substitution of other named substituents for $R_3$–$R_6$, e.g., ethyl, propyl, butyl, methoxy, ethoxy, propoxy, hydroxy, paramethylphenyl, etc. for one or more of the trimethyl or tetramethyl derivatives above named, other correspondingly named N,N'-dichloro, dibromo- or bromochloro-2-imidazolidinone derivatives may be named.

The inorganic salt with which the solid halogen-containing disinfectant, e.g., particulate calcium hypochlorite, may be blended is a salt that is a solid at room temperature, readily water-soluble at ambient temperatures, e.g., 35° F.–105° F. (2° C.–41° C.), and which is compatible with the disinfectant material, e.g., calcium hypochlorite. Examples of such materials include: sodium chloride, potassium chloride, aluminum sulfate, aluminum sulfate hydrate [$Al_2(SO_4)_3 \cdot 18H_2O$], potassium aluminum sulfate and its hydrate, sodium aluminum sulfate and its hydrates, ammonium aluminum sulfate and calcium chloride. Sodium chloride is preferred.

The inorganic salt blended with the calcium hypochlorite should be of a size that permits the salt to quickly dissolve in the water. Inorganic salts in the physical form of flakes dissolve readily in water. Typically, the salt will have a particle size of at least −20 U.S. Sieve (−0.83 millimeters). Preferably, at least 95 percent of the salt to be blended will dissolve in less than about two minutes when added to water having a temperature of about room temperature, e.g., 20°–22° C.

The amount of dyed particulate inorganic salt, e.g., sodium chloride, blended with the particulate halogen-containing material, e.g., calcium hypochlorite, will be that amount that will permit the resultant blended product to be readily identified by visual inspection. Typically, between about 0.1 and about 10 weight percent of the finely-divided dyed inorganic salt is dispersed in the solid, halogen-containing material. More typically, between about 1 and about 5 weight percent of the salt is so dispersed.

The inorganic salt is treated with a water-dispersible colorant (pigment or dye) that is reasonably resistant to attack (usually to oxidation) by the available halogen species in the solid halogen-containing material. By water-dispersible is meant that the colorant may be water-soluble or readily dispersible in water by the action of suitable surface active agents with which the colorant may be formulated. Examples of colorants that may be so used are direct dyes, i.e., azo-group-containing dyes, disperse dyes, e.g., derivatives of 1,4-diamino- or 1,4,5,8-tetraaminoanthraquinones, phthalocyanines and other organic pigments containing sulfonic acid radicals which impart water solubility or a degree of hydrophilic character to the dye. Other colorants that may be used are thioindigo derivatives such as Vat Red 1 (C.I. No. 73360), Vat Red 41 (C.I. No. 73300) and Vat Orange 5 (C.I. No. 73335). Preferred are the phthalocyanine dyes, such as Pigment Blue (C.I. No. 74160), available from Tricon Colors, Inc. as Tricosol Blue 17732, and C.I. Pigment Green 7 (C.I. 74260) available from Tricon Colors, Inc. as Green Shade No. 19089. Preferably, the colorant used is green or blue, a shade of green or blue, or mixtures of green and blue.

The colorant with which the inorganic salt is treated should be reasonably stable in the presence of halogen species present in the solid halogen-containing material, e.g, calcium hypochlorite, with which the treated salt is blended, i.e., the color of the colorant should not fade significantly after 30 days of storage at room temperature in the presence of the halogen-containing material, although the color may change to a different color or shade but remain as a readily discernible color. The oxidative stability of a colorant can be readily determined by applying the colorant to a readily available solid salt, e.g, sodium chloride, in the amounts utilized herein, blending about 2 weight percent of the treated salt with the chosen solid halogen-containing material, e.g., calcium hypochlorite, and storing the blended material at about 22° C. for 30 days. After such period, the dyed salt should still be recognizable as a colored additive to be considered useful.

The inorganic salt may be treated with the water-dispersible colorant in amounts sufficient to provide a distinct and recognizable color to the salt. Treatments which provide between about 0.01 and about 5, more particularly from about 0.1 to about 1, preferably between about 0.4 and 0.8, e.g., 0.7, weight percent of the colorant, based on the weight of the salt, are contemplated.

Any convenient method for treating the inorganic salt with the colorant may be used, i.e., any conventional liquid-solid or solid-solid unit operation may be used. In one embodiment, an aqueous liquid dispersion of the colorant is applied to the surface of the solid inorganic salt in amounts sufficient to treat the salt with the desired level of colorant. Application of the aqueous dispersion of colorant to the solid salt may be accomplished by spraying the salt with the aqueous dispersion or by simply adding the aqueous dispersion to an agitated bed of the salt. Following application of the aqueous colorant dispersion, the treated salt is dried at moderate temperatures in, for example, a circulating oven, to remove the amount of water added with the colorant. Suitably, the treated salt may be dried at 100° F. (38° C.) for three hours. The time and temperature required to remove water added with the colorant are interrelated, i.e., the higher the temperature, the shorter the time required and vice versa. Temperatures that will not degrade the colorant should be chosen and used. Preferably, the highest temperature that can be used without adversely affecting the colorant will be used so as to shorten the time required to dry the treated salt.

In another embodiment, the solid colorant is blended dry with the inorganic salt and subsequently, a small amount of water is added to the resulting blend to more uniformly mix the colorant and salt. Thereafter, the resulting wet mixture is heated at moderate temperatures (as previously described) to remove substantially all of the water added to the treated salt. The substantially dry, colorant-containing salt product is then admixed with the solid halogen-containing material in amounts ranging between about 0.1 and about 10 weight percent. Any convenient solid-solid blending technique, e.g., blender, etc., may be used to disperse the colorant-containing salt substantially uniformly within the solid halogen-containing material.

The compositions of the present invention may be utilized in any water treatment application where the described halogen-containing material, e.g., calcium hypochlorite, is typically used, e.g., in applications requiring a sanitizer, oxidant or disinfectant. For example, they may be used for the treatment of residential swimming pool water. It is conventional to broadcast granular calcium hypochlorite periodically directly on the water in the pool in quantities sufficient to maintain the level of available chlorine in the pool at or above prescribed levels, e.g., from less than 1 part per million to a few parts per million chlorine. When broadcast in this manner, the calcium hypochlorite composition of the present invention functions in the same manner as conventional granular calcium hypochlorite. The salt portion of the water-dispersible colorant-containing salt dissolves in the water and the colorant with which the salt was treated remains dispersed in the water. Because of the small amount of colorant used in the case of a blue or green colorant, there is no substantial change in the color of the pool water. The dispersed colorant is removed from the pool water by conventional filtering apparatus through which the pool water is passed.

Granular or particulate halogen-containing materials that contain colorant-containing salt may also be formed into shaped articles, such as tablets, briquettes, pellets, etc. This may be accomplished by conventional size enlargement apparatus, e.g., tableting presses, by utilizing the compositions of the present invention in place of granular materials typically used to form such articles, i.e., materials that do not contain the colorant treated inorganic salt. These shaped articles, e.g., tablets, may be placed, for examples, in a skimmer or dissolving basket located around a residential swimming pool to provide continuous contact with the pool water. In these and other application methods, the colorant treated inorganic salt dissolves readily in the pool water and the water dispersible colorant is removed by a filter through which the pool water is continuously passed.

The present invention is more particularly described in the following examples, which are intended as illustrative only, since numerous modifications and variations therein will be apparent to those skilled in the art.

EXAMPLE 1

Diamond Alberger flake sodium chloride was dry blended with 0.7 weight percent Tricosol Blue 17732 colorant. A small amount of water was added to the mixture while continuing the blending operation to disperse the colorant over the salt particles. When the mixture was thoroughly blended and the colorant well dispersed, the added water was removed by heating the mixture at 150° F. Similarly, sodium chloride salt was treated with 1 percent Green Shade No. 19089 in the manner previously described. Separate samples of Pittclor® granular calcium hypochlorite, ACL® 60 Chlorinating Compositions [sodium dichloro-s-triazinetrione (sodium dichloroisocyanurate)] and ACU®90 Plus Chlorinating Composition [trichloro-s-triazinetrione (trichloroisocyanuric acid)] were each blended with 10 weight percent of the sodium chloride salt blended with Tricosol Blue 17732. Separate samples were also blended with 10 weight percent of the sodium chloride salt blended with Green Shade No. 19089. The samples were placed in a laboratory oven at 38° C. and periodically observed for any change in the color of the colorant-containing salt granules. Observations are tabulated in Table I.

TABLE I

| Product | Elapsed Time, Days | | | | | | |
|---|---|---|---|---|---|---|---|
| | 7 | 22 | 37 | 47 | 57 | 83 | 105 |
| Tricosol Blue | | | | | | | |
| Calcium Hypochlorite | Dark Green | NC | NC | NC | NC | NC | NC |
| Dichloroisocyanurate | NC | NC | NC | NC | NC | NC | NC |
| Trichloroisocyanuric Acid | NC | NC | NC | NC | NC | NC | NC |
| Green Shade | | | | | | | |
| Calcium Hypochlorite | NC | NC | NC | NC | NC | NC | NC |
| Dichloroisocyanurate | NC | NC | NC | NC | NC | NC | NC |

TABLE I-continued

| Product | Elapsed Time, Days | | | | | | |
|---|---|---|---|---|---|---|---|
| | 7 | 22 | 37 | 47 | 57 | 83 | 105 |
| Trichloroisocyanuric Acid | NC | NC | NC | NC | NC | NC | NC |

NC = No change

The data of Table I show that there was no perceptible change in the color of the dyed sodium chloride salt over a 105 day period for the salt dispersed in dichloroisocyanurate and trichloroisocyanurate. After 7 days, the Tricosol Blue colored sodium chloride salt dispersed in calcium hypochlorite changed to a dark green color and thereafter no further significant change in color was observed.

EXAMPLE 2

Eighty pounds of Diamond Alberger flake salt were dry blended with 250 grams of (about 0.7 weight percent) of Tricosol Blue 17732 colorant. After mixing for about 10-15 minutes, about 900 milliliters of distilled water was sprayed onto the mixture while blending continued. The resulting mixture was homogenized for 15 minutes and then dried for about 3 hours in a 150° F. forced air oven. The treated salt caked during drying. The cakes were passed through a fiberglass screen to yield a uniform small particle size.

The colorant-treated salt was formulated with Pittclor ® granular calcium hypochlorite by dry blending 400 pounds of the calcium hypochlorite and 21 pounds of the salt in a double cone blender for 15-20 minutes. After 25 days of storage at room temperature, the color of the colorant-treated salt in the formulated product was unchanged.

EXAMPLE 3

The procedure of Example 2 was repeated using Diamond Alberger coarse salt treated with about 0.5 weight percent Tricosol Blue 17732 colorant. No change in the color of the salt was observed after storage of the formulated product for 75 days at room temperature.

The procedure of Example 2 was repeated using 2.5 weight percent Diamond Tru-Flake Topping salt treated with about 0.5 weight percent Tricosol Blue 17732 colorant to formulate the calcium hypochlorite. No change in the color of the salt was observed after 70 days storage of the formulated product at room temperature.

Although the present process has been described with reference to specific details of certain embodiments thereof, it is not intended that such details should be regarded as limitations upon the scope of the invention except as and to the extent that they are included in the accompanying claims.

What is claimed is:

1. Solid halogen-containing disinfectant material having dispersed therein a readily discernible amount of particulate inorganic salt treated with from about 0.01 to about 5 weight percent of water-dispersible colorant, said inorganic salt and colorant being resistant to oxidation by halogen of the halogen-containing material.

2. The solid halogen-containing disinfectant material of claim 1 wherein the disinfectant is selected from the group consisting of calcium hypochlorite, lithium hypochlorite, chlorinated isocyanuric acid, halogenated hydantoins, sodium-N-chloro-p-toluenesulfonamide, N,N-dichloro-p-toluenesulfonamide, N-halo-2-oxazolidinones and N,N'-dihalo-2-imidazolidinones.

3. The solid halogen-containing disinfectant material of claim 1 wherein the inorganic salt is selected from the group consisting of sodium chloride, potassium chloride, aluminum sulfate, aluminum sulfate hydrate, potassium aluminum sulfate, sodium aluminum sulfate, ammonium aluminum sulfate and calcium chloride, and the treated inorganic salt is present in the disinfectant material in amounts of from about 0.1 to about 10 weight percent.

4. The solid halogen-containing disinfectant material of claim 1 wherein the colorant is selected from the group consisting of direct dyes, disperse dyes, phthalocyanines, and thioindigo derivatives.

5. The solid halogen-containing disinfectant material of claim 3 wherein the disinfectant material is selected from the group consisting of calcium hypochlorite and chlorinated isocyanuric acid, and the colorant is a phthalocyanine.

6. The solid halogen-containing disinfectant material of claim 5 wherein the inorganic salt is sodium chloride and the colorant is green, blue, or shades of green or blue.

7. The solid halogen-containing disinfectant material of claim 6 wherein from about 1 to about 5 weight percent of particulate sodium chloride treated with from about 0.1 to about 1 weight percent of colorant is dispersed throughout the disinfectant material.

8. Calcium hypochlorite having blended therewith from about 0.1 to about 10 weight percent of particulate inorganic salt treated with from about 0.01 to about 5 weight percent of water-dispersible colorant, said inorganic salt and colorant resistant to oxidation by calcium hypochlorite.

9. The calcium hypochlorite of claim 8 wherein the calcium hypochlorite is in the physical form of a powder, granule, or formed shaped article.

10. The calcium hypochlorite of claim 9 wherein the inorganic salt is sodium chloride and the colorant is a phthalocyanine.

11. The calcium hypochlorite of claim 10 wherein from about 1 to about 5 weight percent of the sodium chloride salt treated with from about 0.1 to about 1 weight percent of phthalocyanine colorant is blended with the calcium hypochlorite.

12. The calcium hypochlorite of claim 11 wherein the salt is in flake form, the colorant is a green or blue phthalocyanine, and the calcium hypochlorite is in the granular or tablet form.

13. A solid shaped article comprising a compressed mixture of the disinfectant material of claim 7.

14. The solid shaped article of claim 13 wherein the article is in the shape of a tablet.

* * * * *